United States Patent
Haran et al.

(10) Patent No.: US 7,868,296 B2
(45) Date of Patent: Jan. 11, 2011

(54) SPECTROSCOPY HAVING CORRECTION FOR BROADBAND DISTORTION FOR ANALYZING MULTI-COMPONENT SAMPLES

(75) Inventors: Frank M. Haran, North Vancouver (CA); Reena Meijer-Drees, New Westminster (CA); Sebastien Tixier, North Vancouver (CA)

(73) Assignee: Honeywell ASCA Inc., Mississauga (CA)

( * ) Notice: Subject to any disclaimer, the term of this patent is extended or adjusted under 35 U.S.C. 154(b) by 172 days.

(21) Appl. No.: 12/413,666

(22) Filed: Mar. 30, 2009

(65) Prior Publication Data

US 2010/0243900 A1 Sep. 30, 2010

(51) Int. Cl.
*G01J 5/02* (2006.01)
(52) U.S. Cl. .................................. 250/339.07
(58) Field of Classification Search ............... 250/339.01–339.15
See application file for complete search history.

(56) References Cited

U.S. PATENT DOCUMENTS

| | | | |
|---|---|---|---|
| 4,957,770 A | 9/1990 | Howarth | |
| 6,074,483 A | 6/2000 | Belotserkovsky et al. | |
| 7,071,470 B2 * | 7/2006 | Nomura et al. | 250/339.13 |
| 7,382,456 B2 | 6/2008 | Tixier et al. | |

* cited by examiner

*Primary Examiner*—David P Porta
*Assistant Examiner*—Kiho Kim
(74) *Attorney, Agent, or Firm*—Jetter & Associates, P.A.

(57) ABSTRACT

A spectroscopic method and spectroscopy system therefrom for analyzing samples. A sample includes a first chemical component that has a characteristic first absorption peak is provided. The sample is irradiated in a measurement waveband proximate to the first absorption peak, and at a first and a second reference waveband where the first chemical component lacks characteristic absorption features. Reflected or transmitted detection data is obtained including a measured power proximate to the first absorption peak and first and second reference powers at the reference wavebands. A plurality of different waveband ratios are evaluated using pairs of detection data to generate a plurality of measured waveband ratio values. A parameter of the first chemical component is then determined by evaluating a multidimensional polynomial calibration equation that relates the parameter of the first chemical component to the plurality of different waveband ratios by substituting the measured waveband ratio values into the calibration relation.

16 Claims, 2 Drawing Sheets

SPECTROSCOPY HAVING CORRECTION FOR BROADBAND DISTORTION FOR ANALYZING MULTI-COMPONENT SAMPLES

FIELD OF THE INVENTION

Embodiments of the invention relate to spectroscopy, and in particular to correction of distortion effects when measuring the absorption spectrum for multi-component samples.

BACKGROUND

Spectroscopy refers to the measurement of a quantity based on the interaction between radiation and matter as a function of wavelength or frequency of the radiation. An optical spectrometer is a device that irradiates a sample and analyzes reflected/scattered or transmitted radiation by frequency (or wavelength) components and by their power or intensities. In general, there are two types of spectrometers, dispersive and non-dispersive (e.g. discrete filter or interferometric).

As known in the art of spectroscopy, there are a variety of effects that can cause broadband distortion of the absorption spectrum. Such effects can include, but are not limited to, optical scattering, broadband absorption, scattering due to surface morphology and/or topology.

SUMMARY

This Summary is provided to comply with 37 C.F.R. §1.73, presenting a summary of the invention to briefly indicate the nature and substance of the invention. It is submitted with the understanding that it will not be used to interpret or limit the scope or meaning of the claims.

Embodiments of the present invention describe spectroscopic methods and spectroscopy systems therefrom for analyzing at least a first chemical component of a multi-component sample. Embodiments of the invention generally utilize spectral measurements at a greater number of wavelengths (or frequencies) generally being >two (2), as compared to conventional single wavelength or occasionally a maximum of two (2) wavelengths (or frequencies) used by conventional spectroscopy instruments and methods. Such measurements at >two (2) measurement wavelengths are input into a multi-parameter polynomial calibration relation to automatically generate parametric (e.g. wt. %) data from the multi-component sample.

The Present Inventors have discovered that using spectral information from one or more reference wavebands which are away from absorption peaks of the first chemical component along with the conventional measure waveband information which is proximate to an absorption peak of the first chemical component, provides the ability to correct for undesirable measurement effects that cause broadband distortion of an absorption spectrum. Such effects include, but are not limited to, optical scattering, broadband absorption, scattering due to surface morphology and/or topology. The multi-component sample can be a liquid, gas or a solid, or be a mixed phase sample (e.g. moisture in a powder).

In embodiments of the invention the multi-component sample includes a first chemical component that has at least a characteristic first absorption peak is irradiated in a measurement waveband proximate to the first absorption peak, and is also irradiated at a first and a second reference waveband where the first chemical component lacks any characteristic absorption features. Reflected or transmitted detection data is detected including a measured power proximate to the first absorption peak and first and second reference powers at the reference wavebands. A plurality of different waveband ratios (WR's) are evaluated using pairs of detection data to generate a plurality of measured WR values. A content of the first chemical component is then determined by evaluating a multidimensional polynomial calibration equation that relates the content of the first chemical component to the plurality of different WR's by substituting the measured WR values for the plurality of different WR's in the calibration relation.

Embodiments of the invention are generally described for measuring parameters for one of the chemical components of the multi-component sample. However, embodiments of the invention can be generally applied to as many different chemical components as are present in the sample, provided as each desired component has a characteristic absorption feature and two (2) reference wavebands measurable by the instrument provided.

The measurement wavebands and reference wavebands are both typically 10-200 nm wide. As used herein, the term "proximate" to the first absorption peak for the "measurement waveband" refers to a spectral location that is within five (5) times the full width at half maximum (FWHM) of the first absorption peak. The term "reference waveband" lacking characteristic absorption features as used herein refers to a spectral location that is generally at least one (1) times the FWHM away from the maximum of the first absorption peak, or other absorption peak(s) of the first chemical component if present. Typically, the reference wavelengths are at least 30 nm from the first absorption peak.

The respective wavelength ranges are typically in the infrared, which is generally between 750 nm and 1 mm, such as the near infrared (NIR) which is generally defined herein as being 0.75-2.0 µm in wavelength. However, assuming the component of interest provides a spectral signature in the UV or visible range, the wavelength range can span from the UV through the full IR range.

Methods according to embodiments of the invention can generally be applied to data generated by any type of spectroscopic sensor, operated in either reflection or transmission mode, using either a spectrometer or discrete filter technology. Benchtop devices such as FTIR spectrometers can also generally be used.

DETAILED DESCRIPTION

Figure 1:
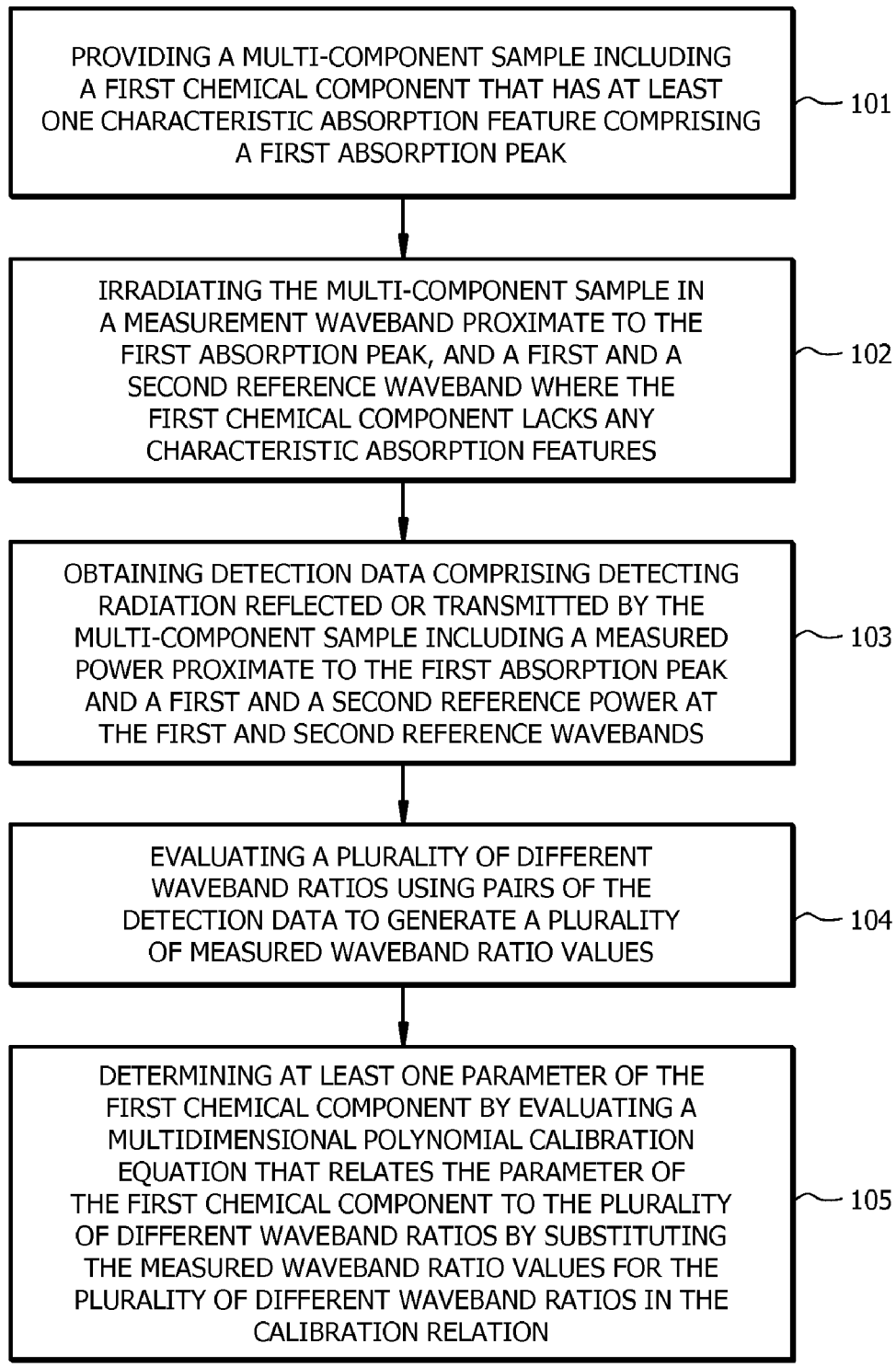
FIG. 1 is a flow chart showing steps in a first exemplary method for measuring a parameter of a first chemical component in a multi-component sample, according to an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention describe spectroscopic systems and related spectroscopic methods for measuring a parameter of a first chemical component in a multi-component sample. In one embodiment, the chemical component of interest is a residual liquid, such as moisture in a solid material (e.g. powder). In another embodiment, the component of interest is a solid component of a multi-solid component sample. In yet another embodiment, the multi-component sample comprises a gaseous mixture.

FIG. 1 is a flow chart showing steps in a first exemplary spectroscopic method 100 for analyzing multi-component samples. In step 101, a multi-component sample including at least a first chemical component that has at least a characteristic first absorption peak is provided. In step 102 the sample is irradiated in a measurement waveband proximate to the first absorption peak, and at a first and a second reference waveband where the first chemical component lacks any characteristic absorption features. As described above, "proximate" to the first absorption peak for the measurement waveband refers to a spectral location that is within five (5) times the FWHM of the first absorption peak, and "reference waveband" lacking characteristic absorption features refers to a spectral location that is generally at least one (1) times the FWHM away from the maximum of the first absorption peak or other absorption peak(s) of the first chemical component, if present.

Step 103 comprises detecting radiation reflected or transmitted including a measured power proximate to the first absorption peak and first and second reference powers at the reference wavebands.

In step 104, a plurality of different waveband ratios (WR's) which serve as variables in the calibration equation described below are evaluated using pairs of the detection data to generate a plurality of measured WR values. The instrument's responses at these wavebands are generally recorded, then combined into the respective WR values. Each WR can be constructed as follows:

$$WR_n = \frac{\text{response at waveband } i}{\text{response at waveband } j}$$

These WR's may combine one or more of reference wavebands, measurement wavebands, and reference/measurement pairs.

Step 105 comprises determining a parameter of the first chemical component by evaluating a multidimensional polynomial calibration equation that relates the parameter of the first chemical component to the plurality of different WR's by substituting the measured waveband ratio values for the WR's into the calibration relation. The calibration relation is generally at least first order in the two (2) or more of the plurality of different WR's, and is generally in the following form:

constituent wt=$A_0+A_1 \times WR_1+A_2 \times WR_1^2+A_3 \times WR_1^3+\ldots+B_1 \times WR_2+B_2 \times WR_2^2+B_3 \times WR_2^3+\ldots+C_1 \times WR_3+C_2 \times WR_3^2+C_3 \times WR_3^3+\ldots$ where $A_i$, $B_i$, etc. are the calibration constants, and $WR_i$ are the variables.

The method can include the step of generating the calibration constants from calibration samples using a non-spectroscopic method for establishing known constituent weights for each of a plurality of calibration samples, such as using a gravimetric method. Spectroscopy is performed to obtain spectroscopic calibration measurements for each of the plurality of calibration samples, followed by curve fitting (e.g. using a suitable fitting algorithm) the spectroscopic calibration measurements to the known constituent weights to obtain the calibration constants $A_i$, $B_i$, etc.

In one embodiment of the invention, the component of interest comprises a liquid. Most liquids have a plurality of absorption peaks. For example, in the NIR, water is known to have absorption peaks at about 1.46 µm (generally referred to herein as 1.4 µm) and 1.93 µm (generally referred to herein as 1.9 µm). A variety of liquids can be measured using embodiments of the invention. Such liquids generally have at least one, and generally a plurality of absorption peaks in the NIR. NIR spectra results from combination and overtone bands of C—H, N—H, O—H vibrations. As described above, the respective wavelength ranges are generally in the infrared, such as the NIR defined above as being from 0.75-2.0 µm in wavelength.

Figure 2:
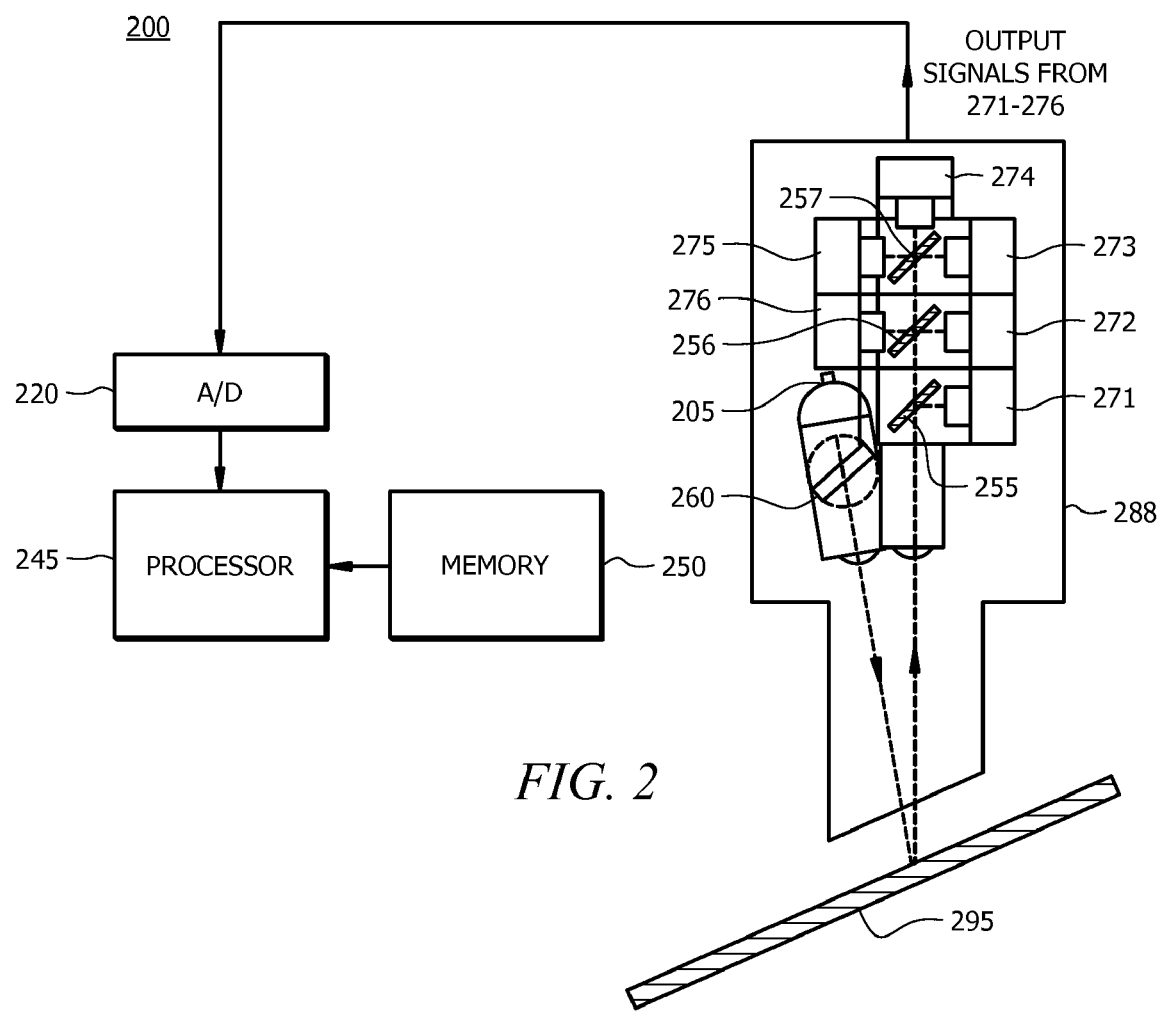
FIG. 2 is a block diagram of a non-dispersive reflection based infrared spectroscopic system having a processor running a multi-parameter fitting equation stored in associated memory run by the processor for automatically generating parameter data for multi-component samples, according to an embodiment of the invention.

FIG. 2 is a simplified block diagram of a non-dispersive reflection based infrared spectroscopic system 200 as known in the art, modified to include a processor 245 running software having a multi-dimension polynomial calibration equation according to an embodiment of the invention. An exemplary non-dispersive reflection based infrared spectroscopic system is disclosed in U.S. Pat. No. 6,074,483 to Belotserkovsky et al, for example. The advantages of such systems include ruggedness, low cost, speed and good signal to noise, so that they are generally ideal for industrial applications.

System 200 is arranged as a reflection system and comprises a detector assembly 288 comprising broadband radiation source 205 including an IR modulator 260 that generally provides at least NIR radiation, a plurality of beam splitters 255-257, and a plurality of discrete filter/detectors 271-276 for measuring different wavelength bands. Multi-component sample is shown as reference 295. Although system 200 is shown having six (6) filter/detectors 271-276 which thus enables measurement of six (6) different wavelengths (e.g. two (2) measure wavelengths and four (4) reference wavelengths), to measure one (1) measure wavelength and two (2) references wavelengths system 200 can be realized with three (3) filter/detectors, and one (1) beam splitter, such as filter/detectors 273-275 and beam splitter 257 shown in FIG. 2.

Output detection signals from the plurality of discrete filter/detectors 271-276 are coupled to an analog to digital (A/D) converter 220, which is generally multi-channel A/D. A/D converter 220 converts the analog detection signals received from filter/detectors 271-276 to digital signals which are then supplied to processor 245 for processing.

The software having the multi-dimension polynomial calibration equation that is associated with processor 240 may be stored as firmware memory 250, such as in ROM. From the digital detection signals provided by A/D converter 220, the stored multi-parameter fitting equation run by the processor 245 automatically generates a parameter (e.g. wt. %) for one or more components of the component of a multi-component sample 295.

An alternate arrangement is a multi-channel spectroscopic system. Such systems generally require as many filters as detectors. However, a single point detector can be used with a filter wheel with typically up to six (6) filters.

Embodiments of the invention may also be practiced in transmission-based systems. Moreover, in some applications FTIR-based system, may be used. However, FTIR spectroscopic systems are generally not used for online sensing due to their known environmental sensitivity (e.g. vibration, temperature swing, etc).

Embodiments of the invention can be applied to help control production processes using generally rapid and reliable methods of quality control that can help improve product quality. Spectroscopy according to embodiments of the invention can replace time consuming traditional methods such as Karl-Fischer titration, loss on drying, and headspace GC analysis with methodologies according to embodiments of the invention that are generally high sensitivity, fast, non-destructive and capable of being implemented in highly automated systems.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

The two (2) examples described below are both done in the near-IR in the 1 to 4 micron wavelength range. The first example uses a fixed-filter spectroscopic sensor operating in transmission mode, and the second example uses a fixed-filter spectroscopic sensor in reflection mode.

Example 1

Measurement of Moisture in White Mineral-Based Powder

In this example, moisture was measured for three (3) different types of powder using a fixed-filter, non-dispersive, reflection mode spectroscopic sensor. The exact nature of the differences between the types of powder are not material to this example, but each led to different scattering behavior, and hence different functional forms of the calibration equation. All data was collected simultaneously at two (2) reference wavelengths (1.3 and 1.8 µm), as well as at the 1.4 µm and 1.9 µm water absorption peaks (measure wavelengths). A three (3) dimensional $2^{nd}$ order fit was defined by the following general equation:

$$M = aX + bY + cZ + dX^2 + eY^2 + fZ^2 + g$$

where M is the moisture content (e.g. wt. % moisture) as measured by the sensor, a, b, c, d, e, f and g are calibration parameters, and X, Y, Z are the WRs (variables). The above equation is 3-dimensional due to the use of three (3) WRs (X, Y and Z), and the equation is second order due to the highest power in the equation being two (2). After establishing the calibration equations for each grade of powder using samples of the same with known moisture content, the moisture content was found to be measurable in random samples of each grade of powder to within 1.5% (2-sigma). In comparison, the moisture measurement of the same material performed using a standard, non-corrective algorithm was found not to be measurable (i.e. a measurement error of over 100% (2-sigma) for each grade of powder.

Example 2

Measurement of Thickness of TiO2-Doped PET

In this example, the total thickness of polyethylene terephthalate sheet, doped with a mineral whitener ($TiO_2$), was measured using a fixed-filter, non-dispersive, transmission mode spectroscopic sensor. The mineral whitener leads to scattering of the near-infrared light and consequent deformation of the absorption spectrum. This scattering was corrected using an algorithm according to an embodiment of the invention. After establishing a calibration relation using samples of known thickness, the total thickness in the range from 25 to 70 microns was measured in random samples with an accuracy of less than 1 micron, generally being within 1.0% (2-sigma). In comparison, the total thickness of the same material performed using a standard non-corrective algorithm was found not to be measurable (i.e. a measurement error of over 100% (2-sigma).

As known in the art, the thickness parameter may be obtained from a mass-per-unit-area parameter which is also known as "basis weight" of component which may be generally measured in all cases. Correlation to thickness as described in Example 2 is made possible if the density of the material is constant, which is true for many industrially-produced materials.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

We claim:

1. A spectroscopic method for analyzing samples, comprising:
   providing a multi-component sample including at least a first chemical component to be analyzed that has at least one characteristic absorption feature comprising a first absorption peak;
   irradiating said multi-component sample with radiation in a measurement waveband proximate to said first absorption peak, and at least a first and a second reference waveband located wherein said first chemical component lacks said characteristic absorption feature;
   obtaining detection data comprising detecting radiation reflected or transmitted by said multi-component sample responsive to said irradiating including a measured power proximate to said first absorption peak and a first and second reference power at said first and said second reference wavebands, respectively;
   evaluating a plurality of different waveband ratios using a plurality of pairs of said detection data to generate a plurality of measured waveband ratio values, and
   determining at least one parameter of said first chemical component by evaluating a calibration relation comprising a multidimensional polynomial equation that relates said parameter of said first chemical component to said plurality of different waveband ratios by substituting said plurality of measured waveband ratio values for said plurality of different waveband ratios.

2. The method of claim 1, wherein said multi-component sample comprises a powder sample comprising said first chemical component and a second chemical component that comprises moisture.

3. The method of claim 1, wherein said radiation comprises UV to mid-IR radiation.

4. The method of claim 3, wherein said radiation comprises near infrared (NIR) radiation.

5. The method of claim 1, wherein said plurality of different waveband ratios include at least one reference waveband ratio including said first reference waveband and said second reference waveband.

6. The method of claim 1, wherein said measurement waveband comprises a first measurement waveband and a second measurement waveband, and said plurality of different waveband ratios include at least one measurement waveband ratio including said first and said second measurement waveband.

7. The method of claim 1, wherein said parameter comprises a content of said first chemical component in said multi-component sample.

8. The method of claim 7, wherein said content comprises a constituent weight and said multidimensional polynomial equation includes a plurality of calibration constants ($A_i$, $B_i$, $C_i$) and variables comprising said waveband ratios ($WR_i$), said multidimensional polynomial equation being in the form of:

$$\text{constituent wt} = A_0 + A_1 \times WR_1 + A_2 \times WR_1^2 + A_3 \times WR_1^3 + \ldots + B_1 \times WR_2 + B_2 \times WR_2^2 + B_3 \times WR_2^3 + \ldots + C_1 \times WR_3 + C_2 \times WR_3^2 + C_3 \times WR_3^3 + \ldots$$

further comprising the step of generating said plurality of calibration constants, comprising:
   using a non-spectroscopic method for establishing known constituent weights for each of a plurality of calibration samples;
   performing spectroscopy to obtain spectroscopic calibration measurements for each of said plurality of calibration samples, and
   curve fitting said spectroscopic calibration measurements to said known constituent weights to obtain said plurality of calibration constants.

9. The method of claim 1, wherein said spectroscopic method comprises reflection mode spectroscopy.

10. The method of claim 1, wherein said spectroscopic method comprises transmission mode spectroscopy.

11. A spectroscopy system for analyzing at least a first chemical component of a multi-component sample that has at least one characteristic absorption feature comprising a first absorption peak, comprising:
   A spectroscopic sensor comprising:
   a broadband radiation source for irradiating said multi-component sample with radiation in a measurement waveband proximate to said first absorption peak, and at least a first and a second reference waveband located wherein said first chemical component lacks said characteristic absorption feature;
   a multi-channel detector for obtaining detection data comprising detecting radiation reflected or transmitted by said multi-component sample responsive to said irradiating including a measured power proximate to said first absorption peak and a first and second reference power at said first and said second reference wavebands, respectively, and
   a processor having associated memory for evaluating a plurality of different waveband ratios using a plurality of pairs of said detection data for generating a plurality of measured waveband ratio values, and determining at least one parameter of said first chemical component by evaluating a calibration relation stored in said memory comprising a multidimensional polynomial equation that relates said parameter of said first chemical component to said plurality of different waveband ratios by substituting said plurality of measured waveband ratio values for said plurality of different waveband ratios.

12. The system of claim 11, wherein said plurality of different waveband ratios include at least one reference waveband ratio including said first reference waveband and said second reference waveband.

13. The system of claim 11, wherein system is configured as a transmissive mode system.

14. The system of claim 11, wherein system is configured as a reflection mode system.

15. The system of claim 11, wherein said broadband radiation source provides near infrared (NIR) radiation.

16. The system of claim 11, further comprising an analog to digital (A/D) converter coupled between an output of said detector and said processor.

* * * * *